United States Patent
Zeyssig et al.

(10) Patent No.: US 11,793,925 B2
(45) Date of Patent: Oct. 24, 2023

(54) METHOD AND DEVICE FOR INTRAOPERATIVE DETERMINATION OF DRAG COEFFICIENT VALUES OF DIFFERENT MEDICAL INSTRUMENTS IN THE USE OF A MEDICAL FLUID PUMP

(71) Applicant: W.O.M. WORLD OF MEDICINE GMBH, Berlin (DE)

(72) Inventors: Andreas Zeyssig, Berlin (DE); Stephan Schulze, Berlin (DE); Ibrahim Ilik, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 813 days.

(21) Appl. No.: 16/339,771

(22) PCT Filed: Oct. 5, 2017

(86) PCT No.: PCT/DE2017/000332
§ 371 (c)(1),
(2) Date: Dec. 30, 2019

(87) PCT Pub. No.: WO2018/064996
PCT Pub. Date: Apr. 12, 2018

(65) Prior Publication Data
US 2020/0147292 A1     May 14, 2020

(30) Foreign Application Priority Data

Oct. 5, 2016   (DE) .......................... 102016011819.9

(51) Int. Cl.
*A61M 3/02*    (2006.01)
*A61M 13/00*   (2006.01)
*A61B 1/015*   (2006.01)

(52) U.S. Cl.
CPC ........ *A61M 3/0216* (2014.02); *A61M 13/003* (2013.01); *A61B 1/015* (2013.01); *A61M 2205/3344* (2013.01)

(58) Field of Classification Search
CPC ........ A61M 2205/3344; A61M 3/0216; A61M 13/003
See application file for complete search history.

(56) References Cited

U.S. PATENT DOCUMENTS

2007/0078370 A1   4/2007  Cemal et al.
2013/0267779 A1*  10/2013 Woolford et al. ..... A61B 1/015
                                                              606/156
2016/0101247 A1*  4/2016  Zeyssig ............... A61M 13/003
                                                              604/26

* cited by examiner

*Primary Examiner* — Katherine H Schwiker
*Assistant Examiner* — Hong-Van N Trinh
(74) *Attorney, Agent, or Firm* — Stuart H. Mayer; Mayer & Williams PC

(57) ABSTRACT

A medical apparatus for supplying fluids into body cavities includes a controllable fluid pump, a memory device, a feed line, a pressure sensor in the feed line, a medical instrument to be connected to the feed line. The pressure measured by the pressure sensor is an input variable of a mathematical estimation system, which mathematically describes a state space, which estimates the actual pressure in the body cavity and controls the output of the pump by means of this estimated value. The resistance coefficients $\zeta 1$ and $\zeta 2$ of the medical instrument required for the estimation of the pressure are determined when starting the pump. The pressure behavior is evaluated for a certain time, therefrom a characteristic curve is determined, and the characteristic curve is stored in a memory device of the pump.

11 Claims, 6 Drawing Sheets

METHOD AND DEVICE FOR INTRAOPERATIVE DETERMINATION OF DRAG COEFFICIENT VALUES OF DIFFERENT MEDICAL INSTRUMENTS IN THE USE OF A MEDICAL FLUID PUMP

BRIEF DESCRIPTION OF THE INVENTION

Subject matter of the present invention is a method for determining the resistance coefficients in particular of different shaft and endoscope combinations when using a medical fluid pump, e.g. in the context of arthroscopy.

In different medical interventions in the body's interior, fluids, e.g. gases or liquids are introduced into the body's interior and are removed therefrom. An example here is arthroscopy, wherein, for example, in the context of an examination of the knee joint or a therapeutic treatment, the knee is irrigated with an irrigation fluid. Another exemplary treatment is laparoscopy, wherein during a therapeutic intervention, gases (e.g. $CO_2$) are introduced into the body's interior. In the context of these procedures, the measurement, the control and mainly the limitation of the pressure in the body's interior is of particular importance. For therapeutic interventions, it is in particular necessary to secure a certain fluid flow, in order, for example, to wash smoke or blood out of the body's interior, simultaneously, however, to limit the pressure, in order not to damage the body tissue. For this purpose, different apparatuses and methods are available.

For avoiding most various drawbacks of prior methods, recently a method and an apparatus directed thereto was presented that determines the internal body pressure during the pump operation particularly precisely (WO 2015/144120), without a pressure sensor in the body cavity being required. In this method, the data of a pressure sensor that is outside of the respective body cavity, is used as a basis for an estimation of the pressure in the body's interior. For the estimation of the internal body pressure, a mathematical model is used that describes the medical overall system consisting, e.g., of pressure controller, controllable pump motor, feed line, pressure sensor, medical feeding device (e.g., shaft with endoscope), body cavity and, if applicable, fluid outlet (e.g., suction device) by a set of differential equations and combines them in a so-called state space model. Details are described in WO 2015/144120.

As has been found during the operation of such a system, many of the estimation-critical parameters of the individual components described above are substantially constant. It has been found, however, that the different medical feeding devices (e.g., the various possible shafts) exhibit very different parameters, in particular flow parameters. Depending on the used combination of shaft and endoscope (in the following also: instrument), a very different pressure drop will occur.

For the operation of the medical liquid pump, therefore, before beginning an operation, the respective resistance coefficient (see below) has to be measured for each instrument. This can be made, for example, such that in the context of an "open-flow measurement", a liquid flow is generated and the pressure drop relative to the ambient pressure is measured. The measurement takes place, of course, outside of the joint. The obtained flow pressure corresponds to the instrument pressure, i.e., the resistance coefficient of the underlying combination of shaft and endoscope. The disadvantages of this measurement methodology are obvious: The most important disadvantage of this measurement method is that with each change of instrument—i.e., in the case of an intraoperative change of instrument—such a measurement has to be carried out. Disadvantageous, herein, is in particular the required time that is at least 15 to 30 seconds.

Further, it is disadvantageous that a certain amount of fluid has to be used for the measurement, which cannot further be used. This requirement of time and fluid is only difficultly tolerated by the medical practitioners working with such systems.

When the pressure along the fluid flow between two specific system points is considered, then, with identical flow speeds and constant density, the relationship shown in equation 1 will result:

$$\Delta p = p_1 - p_2 \qquad \text{Equation 1:}$$

For instance, $\Delta p$ describes the pressure drop across the used combination of shaft and endoscope (the so-called instrument pressure) from the difference of flow pressure in the hose and the stagnation pressure in the joint. The stagnation pressure in the joint is the variable of the pump to be controlled and is not measured for the reasons mentioned above. In order to determine the pressure in the joint, the instrument pressure has to be measured, in addition to the measurable flow pressure. For this purpose, a characteristic curve can be determined that is based on the dimensionless resistance coefficients $\zeta_1$ and $\zeta_2$ according to equation 2:

$$\Delta p = \zeta_1 \cdot n_1^2 + \zeta_2 \cdot n_1 \qquad \text{Equation 2:}$$

By using equation 2 in equation 1 and re-arrangement with regard to $p_2$, the following statistical measurement equation 3 will follow:

$$(\hat{p}_2) = p_1 - (\zeta_1 \cdot n_1^2 + \zeta_2 \cdot n_1) \qquad \text{Equation 3:}$$

Herein, the left-hand side of equation $(\hat{p}_2)$ represents an estimation of the joint pressure. In order to determine the resistance coefficients of equation 2, at least three pairs of values ($\Delta p$) have to be recorded for three different flows ($n_1$). Such a measurement is illustrated in FIG. 1. Herein, three different flows are adjusted, and the respective pressure differential is measured. As shown in FIG. 1 (top), after a certain time, a stationary final value is obtained. The adjustment of the flow takes place by control of the motor speed of the pump. The determination of the pressure takes place in an open-flow mode, i.e., relative to the ambient pressure.

The methodology mentioned above has some disadvantages:
1) In order to obtain as precise resistance coefficients as possible, it has to be waited, respectively, until the signal has reached the stationary final value.
2) For the identification of the resistance coefficients, at least three speed ranges have to be started, otherwise there will be no solutions for the underlying system of equations.
3) Due to the required time for the adjustment of the stationary final value in combination with the required speed ranges, a duration capable of being improved for the application of the instrument recognition outside of the joint will result.
4) The procedure is not suitable to carry out an identification of the instrument (i.e., the determination of the instrument pressure) in the joint. This would lead to too high an overpressure in the joint.
5) The fluid required for the measurement is not used for the operative measure.

SUMMARY OF THE INVENTION

It is the object of the present invention, therefore, to simplify the measurement of the resistance coefficients for the different instruments. The measurement is to be faster and principally in the body (e.g., in the joint) and to consume as little fluid or gas as possible.

The solution of this object is achieved by the method of claim 1, namely a method for determining and controlling the internal body pressure in medical methods, wherein, as shown in FIG. 7, a fluid is pumped from a fluid source 2, by a controllable pumping device 4 through a feed line 3 into a body cavity 6, wherein the feed line 3 contains, at its patient's end, an exchangeable medical instrument 7, through which the feed of the fluid into the body cavity 6 takes place, wherein the fluid can flow out of the body cavity 6 through at least one second line 8, wherein the pump 4 included in the pumping device is controlled, wherein at least the feed line 3 contains a pressure sensor 5 that measures the pressure in the line 3, wherein the pressure measured by the pressure sensor 5 is an input variable of a mathematical estimation system, which mathematically describes a state space, which estimates the actual pressure in the body cavity and controls the output of the pump by means of this estimated value, characterized by that the resistance coefficients $\zeta_1$ and $\zeta_2$ of the medical instrument required for the estimation of the pressure are determined by that when starting the pump, the pressure behavior is evaluated for a certain time, therefrom a characteristic curve is determined, and the characteristic curve is stored in a memory device 9 of the pump.

The method according to the invention determines the resistance coefficients $\zeta_1$ and $\zeta_2$ already at a one-time start of the pump with acceptable accuracy. A higher accuracy is achieved, when the starting is carried out several times. As an optimum, the two-time start of the pump has been found.

The term "starting the pump" comprises in particular the change of the pump output from 0 ml/min to a pump output adapted to the desired instrument and the intended use (e.g., 25 l/min for insufflation or 500 ml/min for arthroscopy), e.g. by integrating a peristaltic roller pump under adjustment of a target speed. In special cases, the measurement can also be carried out in a manner that the pump is changed from a small output to a significantly larger output (e.g., from 2.5l/min to 25l/min for insufflation or from 50 ml/min to 500 ml/min for arthroscopy). This is also included in the term "starting the pump". Such an embodiment being less preferred requires the adaptation of the calculations presented below, in particular of the calculation of the pressure loss term Δp.

DETAILED DESCRIPTION OF THE INVENTION

The solution of the above object is achieved, further, by the apparatus of claim 6, namely by a medical apparatus for supplying fluids into body cavities, including a controllable fluid pump, a memory device, a feed line, a pressure sensor in the feed line, a medical instrument to be connected to the feed line, characterized by that the pressure measured by the pressure sensor is an input variable of a mathematical estimation system, which mathematically describes a state space, which estimates the actual pressure in the body cavity and controls the output of the pump by means of this estimated value, wherein the resistance coefficients $\zeta_1$ and $\zeta_2$ of the medical instrument required for the estimation of the pressure are determined by that when starting the pump, the pressure behavior is evaluated for a certain time, therefrom a characteristic curve is determined, and the characteristic curve is stored in a memory device of the pump.

Figure 1:
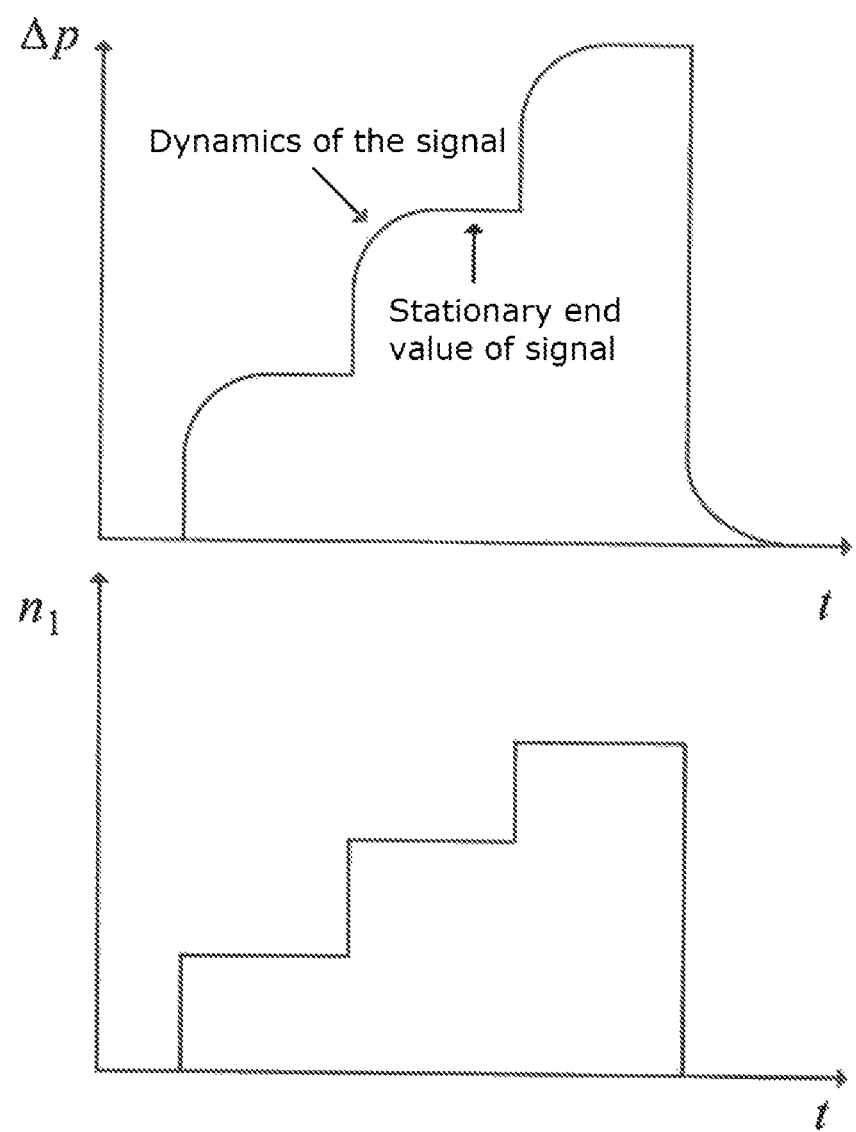
FIG. 1 shows the resistance coefficients of equation 2, at least three pairs of values (Δp) have to be recorded for three different flows (n1).
Figure 2:
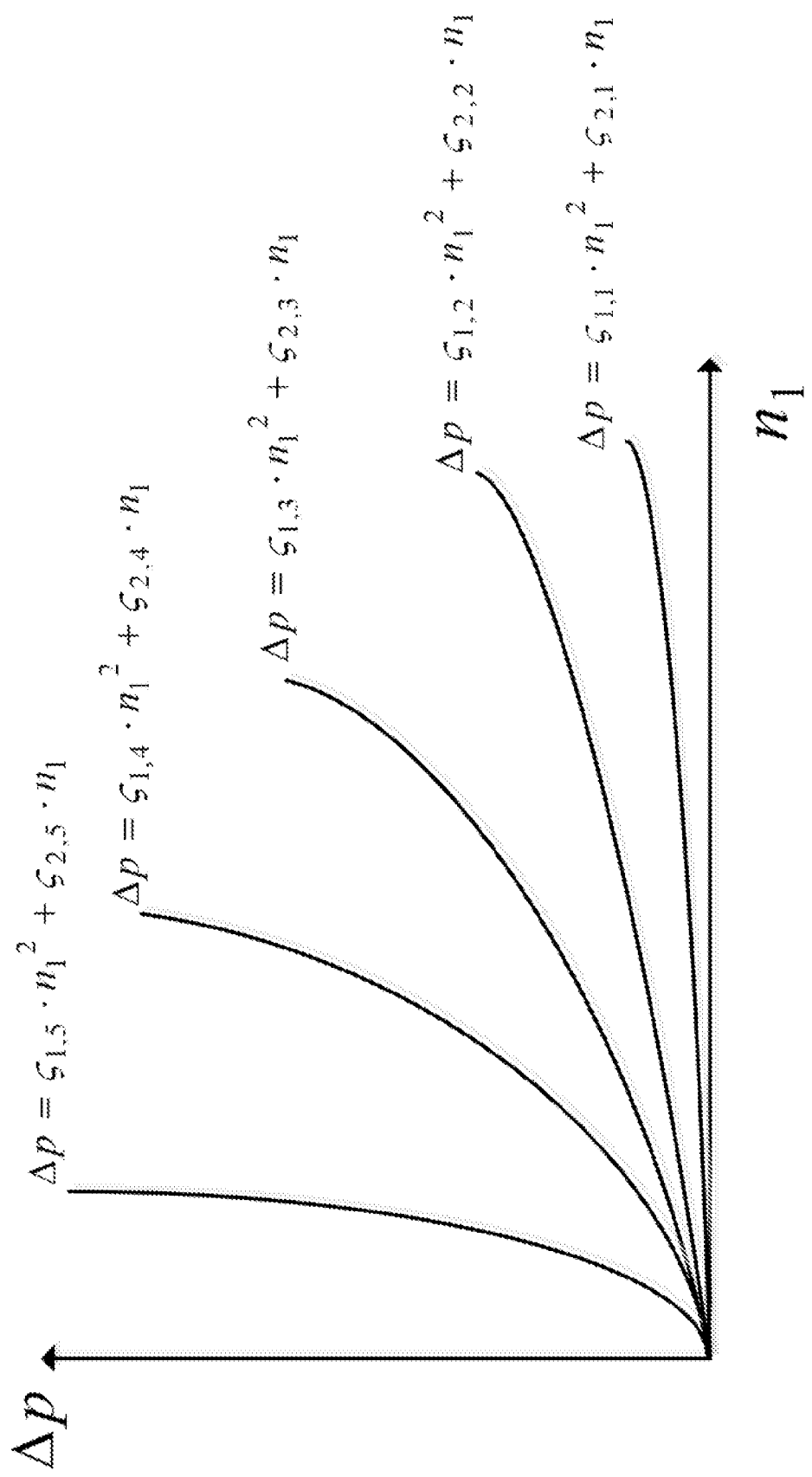
FIG. 2 shows a plurality of characteristic curves that shows such characteristic curves of different instruments.

In order to compensate for the disadvantages of the open-flow method mentioned above, therefore, the following measurement approach is suggested:

For a given medical liquid pump, in a first test series, a plurality of characteristic curves is recorded. For this purpose, the instruments provided for the operation of the liquid pump (i.e., the combinations of shaft and endoscope) are coupled to the pump, and the respective flow-dependent instrument pressure is measured and evaluated. The values measured for a certain instrument can be represented as a characteristic curve. A plurality of characteristic curves that shows such characteristic curves of different instruments, is exemplarily illustrated in a simplified form in FIG. 2. It can be seen that the different resistance characteristics of the instruments mainly depend on the effective flow cross-section. It can be assumed that other physical dependencies will behave in a time-invariant manner. As a result, different resistance coefficients ($\zeta_{1,z}$ and $\zeta_{2,z}$) depending on the flow cross-section are obtained, wherein z is the number of recorded characteristic curves. From these characteristic curves, the $\zeta_2$ values are stored in a memory device of the pump as a priori knowledge.

For measuring and storing the characteristic curves, different ways are considered. It is possible that, when manufacturing the pump, all approved instruments are measured, and the resistance coefficients or the characteristic curves are stored. In another embodiment, prior to each application, i.e., after connecting the respective instrument to the pump, a measurement and storage process of the resistance coefficients or the characteristic curves is carried out. It is also possible, of course, that the pump is available on the market with some stored characteristic curves, but the user can also additionally measure, for his or her preferred instruments, the resistance coefficients or the characteristic curves individually and store them in addition to the already stored data.

In any case, before or during an operation, the measurement process can newly be started, so that adaptations are intraoperatively possible.

In order to derive an algorithm for the instrument recognition in the body (e.g., in the joint), the polynomial described in equation 2 is modified as follows:

$$\varsigma_1 = \frac{\Delta p - \varsigma_2 \cdot n_1}{n_1^2} = \frac{(p_1 - p_2) - \varsigma_2 \cdot n_1}{n_1^2} \quad \text{Equation 4}$$

Equation 4 describes the flow resistance $\varsigma_1$ as a function of the measurable speed, of the measurable flow pressure $p_1$, of the not measurable stagnation pressure $p_2$ in the body and of a predetermined value for the flow resistance $\varsigma_2$. The flow resistance $\varsigma_2$ is assumed as being constant within certain speed ranges. By a short, constant speed supply, a suitable $\varsigma_2$ value is obtained by means of the pressure rise, said $\varsigma_2$ value being selected from the memory.

Figure 3:
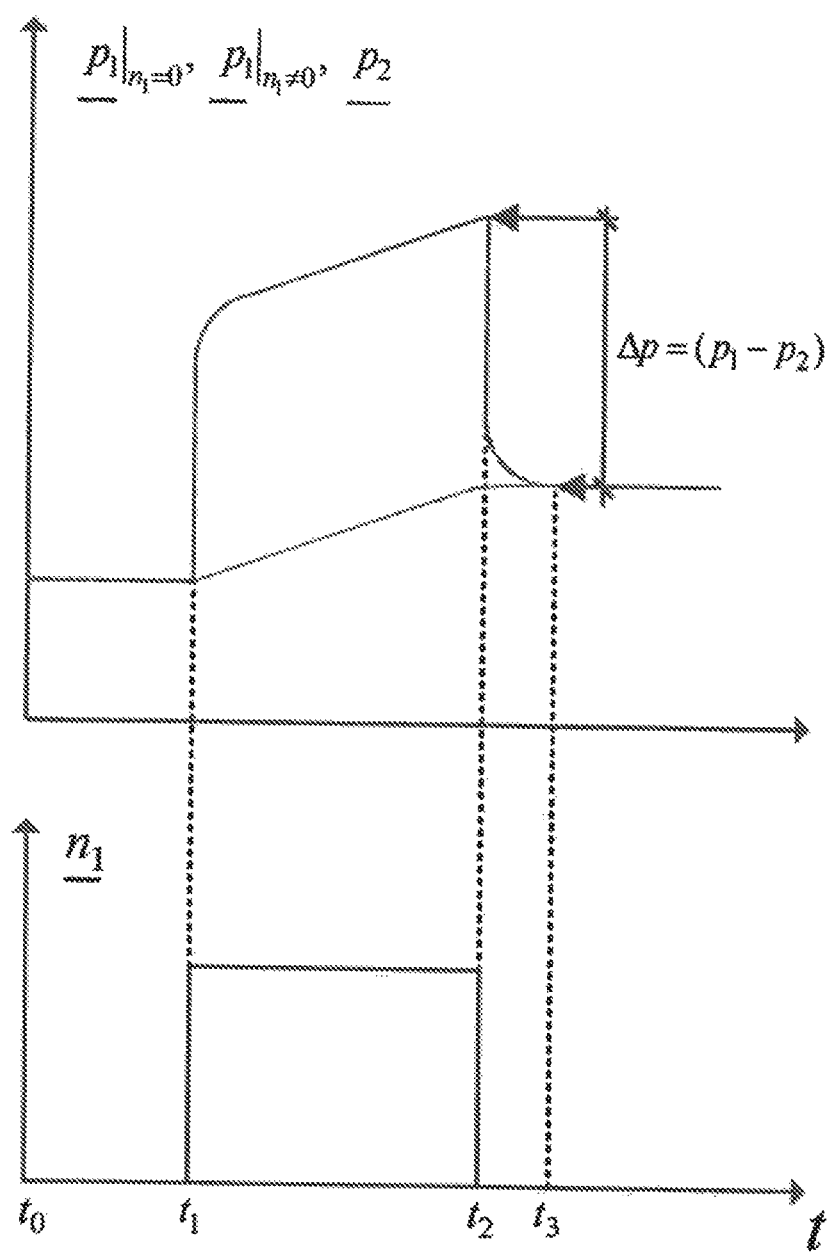
FIG. 3 shows the calculation $\zeta_1$ by means of equation 4, and the loss term Δp.

In order to be able to calculate $\varsigma_1$ by means of equation 4, the loss term $\Delta p$ has to be determined. This is described by means of FIG. 3:

For the calculation of the pressure loss term $\Delta p$, the following conditions apply:

$p_1 = p_2$ for $n_1 = 0$ in the time period $(t_1-t_0)$ and $t_3 > 0$
$p_1 = \Delta p + P_2$ for $n_1 > 0$ Under consideration of the mentioned conditions, at time $t_2$, the measurable flow pressure can be determined. The determination of the stagnation pressure $p_2$ takes place for times $t \geq t_3$, after the dynamics of the measurement signal has dropped. The loss term results from the difference $(p_1-p_2)$.

It has to be taken into account that the accuracy of the calculation of $\Delta p$ depends on the amount of a potential leakage. In the case that the determined instrument parameters are outside of a plausible range, a characteristic curve stored in the memory is selected.

A comparison of the method according to the invention to the prior art method described above shows the surprising advantages of the present invention:

The previous method (open-flow method) requires for determining the resistance coefficients $\varsigma_1$ and $\varsigma_2$, the adjustment of three different flows for the pump. In comparison, the method according to the invention requires only a one- or two-time start of the pump.

The prior art identification method takes 15 to 30 seconds, whereas the method according to the invention (with a two-time start of the pump) requires only about 7 seconds.

The prior art identification method has to be carried out outside of the body. The identification method according to the invention is, as a standard, carried out inside of the body, may however also carried out outside of the body.

The prior art identification method requires time. The user has to wait during the process, until he or she can begin with the intervention. The method according to the invention is running during the application in the background, whereby the user is not affected.

After the prior art identification method, the surgeon cannot immediately begin with the intervention. For this purpose, he or she has first to generate a certain fluid flow in the body's interior (before distension). In the context of the method according to the invention, the fluid flow produced for identification is already used for pre-distension of the body cavity, as a standard. The amount of unused fluid is thus minimized.

Figure 5:
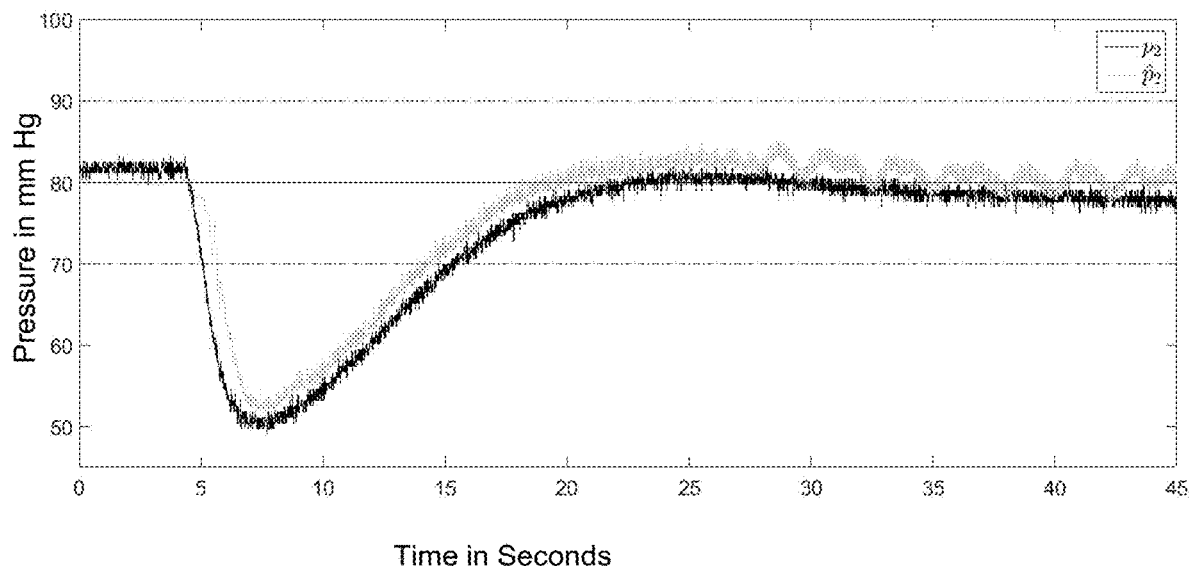
FIG. 5 shows the data of an actual pressure measurement in a joint dummy (shown in black) compared to the estimated data of a system according to WO2015/144120 (shown in gray).
Figure 6:
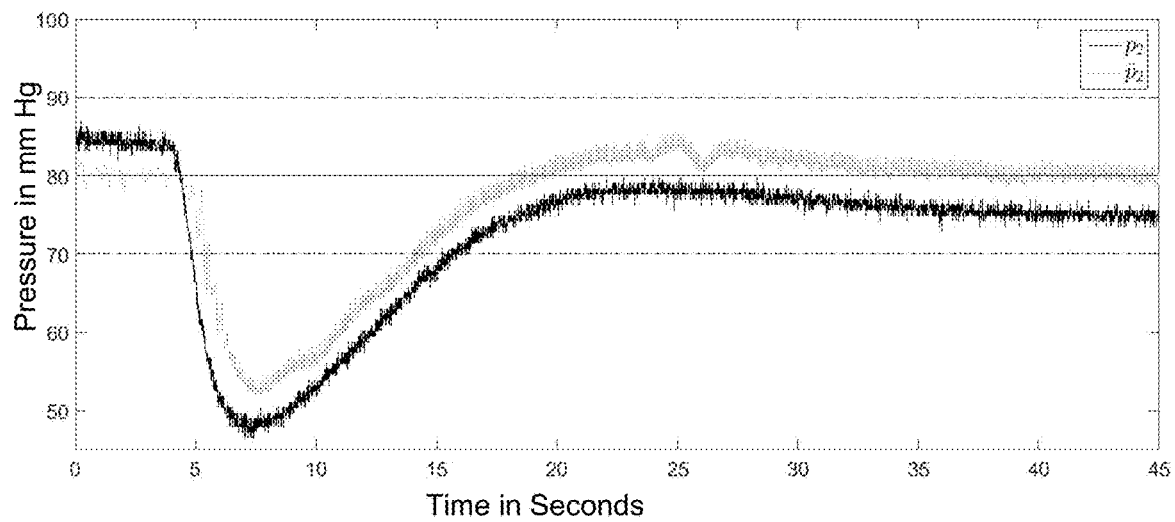
FIG. 6 shows the data of an actual pressure measurement in a joint dummy (shown in black) compared to the estimated data of a system according to the invention (shown in gray).
Figure 7:
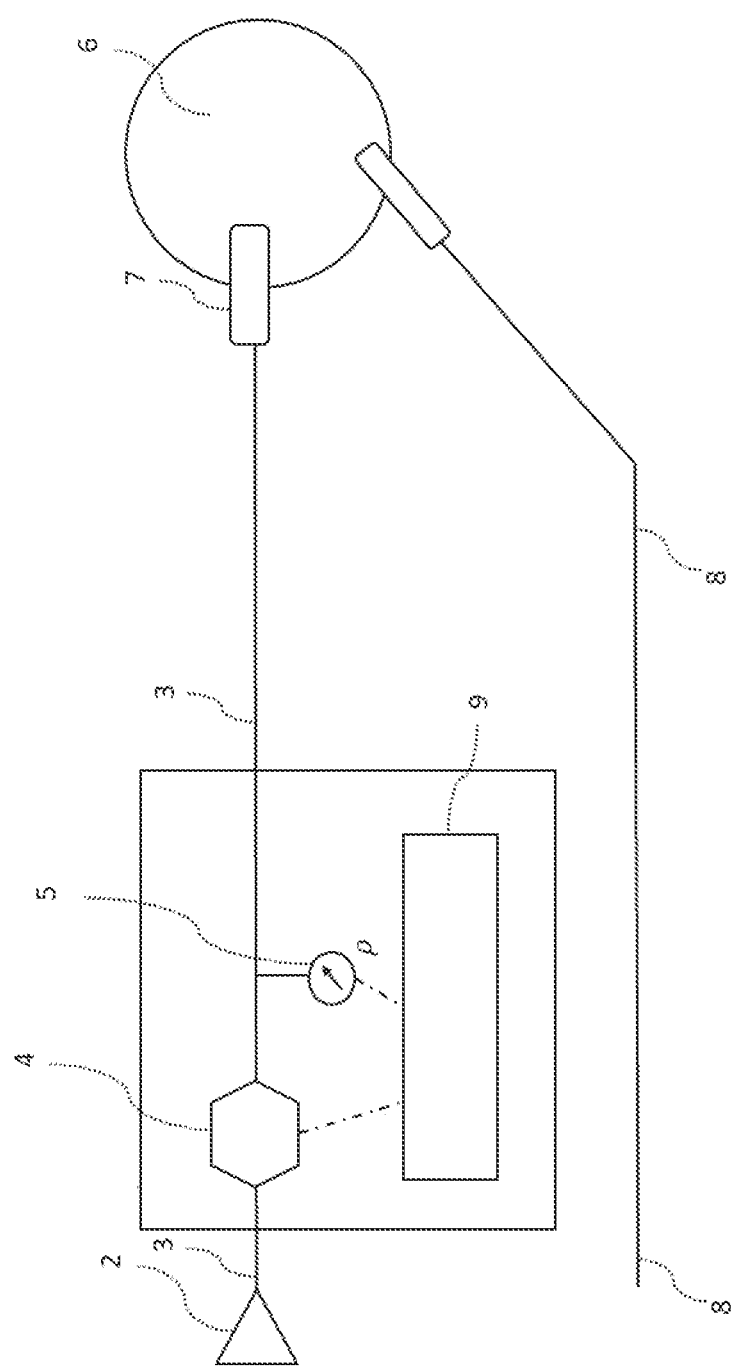
FIG. 7 shows a method for determining and controllimg the internal body pressure in medical methods.

Overall there are, therefore, substantial advantages with regard to the speed and the user friendliness. It is of particular importance that the accuracy of the method according to the invention corresponds approximately to the accuracy of the method known from prior art. FIG. 5 shows the data of an actual pressure measurement in a joint dummy (shown in black) compared to the estimated data of a system according to WO2015/144120 (shown in gray). The actual values are never larger than the estimated values, usually they are slightly smaller than the estimated data, which is preferred for safety reasons. FIG. 6 shows the data of an actual pressure measurement in a joint dummy (shown in black) compared to the estimated data of a system according to the invention (shown in gray). Here, too, the actual values are never larger than the estimated values, usually they are also slightly smaller than the estimated data, which is here, too, preferred for safety reasons. As a result, an approximately comparable accuracy of the pressure estimation in the joint can be seen.

The present invention also relates to an apparatus for carrying-out the method according to the invention, namely a medical fluid pump for irrigating body cavities (e.g., joint cavities). This may be a liquid pump, as well as an insufflator. A liquid pump that operates in the way of a peristaltic roller pump is preferred according to the invention. The controlled pump supplies a fluid through a hose and a medical instrument, for example, a shaft with an optical system into a body cavity, for example, a knee joint. The body cavity may comprise a device for discharge of liquid. The pump is operated, as intended, such that it generates an overpressure in the body cavity that widens (distends) the body cavity. In the apparatus according to the invention, the internal body pressure, as explained above, is determined by way of an estimation. A pressure sensor located outside of the body cavity in or at the hose determines pressure data that represent the input parameter for an estimation. This mathematical estimation system describes a state space, which estimates the actual pressure in the body cavity and controls, by means of this estimated value, the output of the pump. Such an apparatus is described in WO 2015/144120. The apparatus according to the invention includes, in addition to the pump described, an additional memory in which the results of the a priori knowledge are stored.

The memory device can be implemented in an unchangeable chip (e.g., an EPROM). Alternatively, of course, other, in particular exchangeable or modifiable memory media can be considered. It may be provided that the memory device or the stored data can be modified by updates, for example, by exchange of the memory device or by loading new data via corresponding interfaces. Loading new data may optionally also be made via the internet, wherein, of course, the safety of the loading operation has to be secured, in particular with regard to the authenticity of the data source.

For determining the a priori knowledge of the characteristic curves, the pump manufacturer can, for example, measure all instruments provided for the pump (i.e., all combinations of shaft and endoscope) and store these measurement data in the memory device of every pump before shipping.

Alternatively and/or additionally, measurement data can be provided, wherein different instruments are simulated by a proportional valve. This is possible since, as explained above, the different resistance characteristics of the instruments mainly depend on the effective flow cross-section that can be simulated by different settings of a proportional valve.

Alternatively and/or additionally, the resistance coefficients $\varsigma_1$ and $\varsigma_2$ provided by measurements of the instruments can be stored in the memory device of every pump. As soon as the pump is put in operation, the data of the pressure sensor, i.e., the pressure obtained in the hose, are compared to the stored characteristic values. Those resistance coefficients with the largest possible match with the measurement data are selected, and the resistance coefficients $\zeta_1$ and $\zeta_2$ are used in the context of the estimation system for the estimation of the body's internal pressure.

Figure 4:
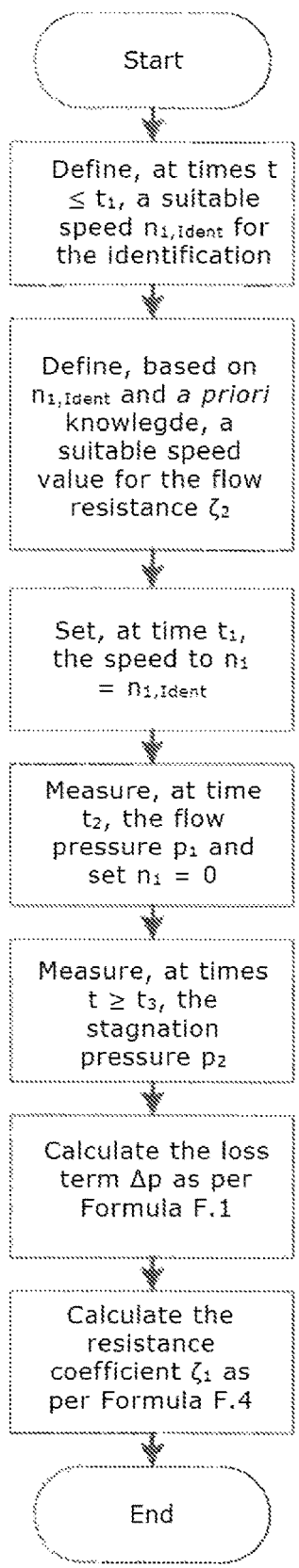
FIG. 4 shows a potential sequence of the program of the invention.

A potential sequence of the program is shown in FIG. 4.

The method according to the invention and the apparatus according to the invention can be operated with different fluid discharge devices. It is possible to secure the discharge from the body cavity through an opening (e.g., an incision) or a hose in a passive manner. It is also possible to provide a pump that pumps the fluid out of the body cavity. Preferred are pump systems with two peristaltic hose pumps (double-roller pumps), of which one roller pump secures the inlet (conveyer pump) and the other one secures the outlet (suction pump). The system according to the invention also operates with several discharge systems.

The method according to the invention and the apparatus according to the invention can be used in particular with liquid pumps in arthroscopy, urology, hysteroscopy, laparoscopy or for examinations of the backbone. Furthermore, insufflators can be operated by means of the method according to the invention and the apparatus according to the invention.

Improvements According to the Invention

An improvement of the apparatus according to the invention is that the resistance coefficients of every instrument are stored on the instrument itself or can be determined by means of the latter. Thus, for example, it is conceivable to attach a transponder at every instrument, which contains data. By a corresponding transceiver at the pump, these data can be read. The data of the instrument can immediately include the resistance coefficients. Alternatively, they may also be identification data, by means of which the resistance coefficients can be retrieved, e.g., from the pump manufacturer via the internet. Furthermore, alternatively, the data can also be stored on other media, e.g., on barcodes that can be designed in a multi-dimensional manner, or magnetic tapes.

The invention claimed is:

1. A method for determining and controlling an internal body pressure in medical procedures,
wherein a fluid is pumped by a controllable pumping device through a feed line into a body cavity,
wherein the feed line contains, at its patients end, an exchangeable medical instrument, through which a feed of the fluid into the body cavity takes place,
wherein the fluid flows out of the body cavity through at least one second line,
wherein a pump included in the controllable pumping device is controlled,
wherein at least the feed line contains a pressure sensor that measures a pressure in the feed line,
wherein the pressure measured by the pressure sensor is an input variable of a mathematical estimation system, which mathematically describes a state space, which estimates an actual pressure in the body cavity and controls an output of the pump by means of this estimated value, wherein resistance coefficients $\zeta 1$ and $\zeta 2$ of the exchangeable medical instrument required for the estimation of the pressure are determined by that when starting the pump, a pressure behavior is evaluated for a certain time, therefrom a characteristic curve is determined, and the characteristic curve is stored in a memory device of the pump, wherein
the resistance coefficient $\zeta 1$ is determined as a function of a measurable speed, a measurable flow pressure $p_1$, a non-measurable stagnation pressure $p_2$ in the body, a pre-determined value for the resistance coefficient $\zeta 2$, and a flow rate $n_1$ that is controlled by a speed of the pump according to the following equation:

$$\zeta_1 = \frac{\Delta p - \zeta_2 \cdot n_1}{n_1^2} = \frac{(p_1 - p_2) - \zeta_2 \cdot n_1}{n_1^2}$$

under consideration of a loss term $\Delta p$ such that $p_1 = \Delta p + p_2$ for $n_1 > 0$, the resistance coefficient $\zeta 2$ being constant within certain speed ranges.

2. The method of claim 1, wherein determining the resistance coefficients $\zeta 1$ and $\zeta 2$ takes place by starting the pump twice.

3. The method of claim 1, wherein determining the resistance coefficients $\zeta 1$ and $\zeta 2$ of the exchangeable medical instrument takes place pre- or intraoperatively.

4. The method of claim 1, wherein the mathematical estimation system is configured in the manner of a Kalman filter.

5. The method of claim 1, wherein the fluid is a gas or a liquid.

6. A medical apparatus for supplying fluids into body cavities,
including a controllable fluid pump, a memory device of the controllable fluid pump, a feed line, a pressure sensor in the feed line, a medical instrument to be connected to the feed line, wherein
a pressure measured by the pressure sensor is an input variable of a mathematical estimation system, which mathematically describes a state space, which estimates an actual pressure in the body cavity and controls an output of the controllable fluid pump by means of this estimated value,
wherein resistance coefficients $\zeta 1$ and $\zeta 2$ of the medical instrument required for the estimation of the pressure are determined by that when starting the controllable fluid pump, a pressure behavior is evaluated for a certain time, therefrom a characteristic curve is determined, and the characteristic curve is stored in the memory device of the controllable fluid pump,
wherein at least one microprocessor, at least one memory and at least one software are configured to carry out the method of claim 1.

7. A medical apparatus for supplying fluids into body cavities,
including a controllable fluid pump, a memory device of the controllable fluid pump, a feed line, a pressure sensor in the feed line, a medical instrument to be connected to the feed line, wherein
a pressure measured by the pressure sensor is an input variable of a mathematical estimation system, which mathematically describes a state space, which estimates an actual pressure in the body cavity and controls an output of the controllable fluid pump by means of this estimated value,
wherein resistance coefficients $\zeta 1$ and $\zeta 2$ of the medical instrument required for the estimation of the pressure are determined by that when starting the controllable fluid pump, a pressure behavior is evaluated for a certain time, therefrom a characteristic curve is determined, and the characteristic curve is stored in the memory device of the controllable fluid pump, wherein
the resistance coefficient $\zeta 1$ is determined as a function of a measurable speed, a measurable flow pressure $p_1$, a non-measurable stagnation pressure $p_2$ in the body, a pre-determined value for the resistance coefficient $\zeta 2$, and a flow rate $n_1$ that is controlled by a speed of the controllable fluid pump according to the following equation:

$$\zeta_1 = \frac{\Delta p - \zeta_2 \cdot n_1}{n_1^2} = \frac{(p_1 - p_2) - \zeta_2 \cdot n_1}{n_1^2}$$

under consideration of a loss term $\Delta p$ such that $p_1 = \Delta p + p_2$ for nl>0, the resistance coefficient $\zeta 2$ being constant within certain speed ranges.

8. The medical apparatus of claim 7, wherein the at least one memory contains data with the resistance coefficients of at least one instrument characteristic curve.

9. The medical apparatus for supplying fluids into body cavities of claim 7, wherein the medical apparatus is an insufflator.

10. The medical apparatus for supplying fluids into body cavities of claim 7, wherein the medical apparatus is a liquid pump for arthroscopy, urology, hysteroscopy, laparoscopy, or for examinations of the backbone.

11. The medical apparatus for supplying fluids into body cavities of claim 7, wherein the medical apparatus is a liquid pump with an integrated conveyer and suction pump.

\* \* \* \* \*